(12) United States Patent
Racenet et al.

(10) Patent No.: US 8,328,064 B2
(45) Date of Patent: Dec. 11, 2012

(54) PIN LOCKING MECHANISM FOR A SURGICAL INSTRUMENT

(75) Inventors: Danyel Racenet, Middletown, CT (US); Dino Kasvikis, Middletown, CT (US)

(73) Assignee: Covidien LP, Mansfield, MA (US)

( * ) Notice: Subject to any disclaimer, the term of this patent is extended or adjusted under 35 U.S.C. 154(b) by 282 days.

(21) Appl. No.: 12/753,998

(22) Filed: Apr. 5, 2010

(65) Prior Publication Data

US 2010/0282818 A1    Nov. 11, 2010

Related U.S. Application Data

(60) Provisional application No. 61/175,815, filed on May 6, 2009.

(51) Int. Cl.
*A61B 17/068* (2006.01)

(52) U.S. Cl. .................... 227/180.1; 227/19; 227/176.1; 227/175.2

(58) Field of Classification Search .................... 227/19, 227/176.1, 175.1, 180.1, 175.2, 175.3
See application file for complete search history.

(56) References Cited

U.S. PATENT DOCUMENTS

| | | |
|---|---|---|
| 2,891,250 A | 6/1959 | Fagge |
| 3,080,564 A | 3/1963 | Strekopitov et al. |
| 3,252,643 A | 5/1966 | Strekopitov et al. |
| 3,269,630 A | 8/1966 | Fleischer |
| 3,275,211 A | 9/1966 | Hirsch et al. |
| 3,315,863 A | 4/1967 | O'Dea |
| 3,494,533 A | 2/1970 | Green et al. |
| 3,589,589 A | 6/1971 | Akopov |
| 3,692,224 A | 9/1972 | Astafiev et al. |
| 3,795,034 A | 3/1974 | Strekopytov et al. |
| 3,822,818 A | 7/1974 | Strekopytov et al. |
| 3,935,981 A | 2/1976 | Akopov et al. |
| 3,949,923 A | 4/1976 | Akopov et al. |
| 4,047,654 A | 9/1977 | Alvarado |
| 4,216,891 A | 8/1980 | Behlke |
| 4,244,372 A | 1/1981 | Kapitanov et al. |
| 4,296,881 A | 10/1981 | Lee |
| 4,305,539 A | 12/1981 | Korolkov et al. |
| 4,354,628 A | 10/1982 | Green |
| 4,378,901 A | 4/1983 | Akopov et al. |
| 4,383,634 A | 5/1983 | Green |
| 4,402,444 A | 9/1983 | Green |
| 4,415,112 A | 11/1983 | Green |
| D273,513 S | 4/1984 | Spreckelmeier |
| 4,442,964 A | 4/1984 | Becht |
| 4,470,533 A | 9/1984 | Schuler |
| 4,475,679 A | 10/1984 | Fleury, Jr. |
| 4,485,811 A | 12/1984 | Chernousov et al. |
| 4,506,670 A | 3/1985 | Crossley |
| 4,506,671 A | 3/1985 | Green |
| 4,508,253 A | 4/1985 | Green |
| 4,522,327 A | 6/1985 | Korthoff et al. |
| 4,527,724 A | 7/1985 | Chow et al. |
| 4,530,453 A | 7/1985 | Green |
| 4,550,870 A | 11/1985 | Krumme et al. |

(Continued)

*Primary Examiner* — Scott A. Smith

(57) ABSTRACT

A surgical instrument comprising a handle portion, an elongated portion defining a longitudinal axis and extending distally from the handle portion, and first and second jaw members dimensioned to clamp tissue therebetween. The first jaw member has at least one row of fasteners arranged in a row substantially transverse to the longitudinal axis. A pin is disposed in mechanical cooperation with the first jaw member and is movable between a first position where the engagement section is spaced from the second jaw member and a second position where the engagement section engages the second jaw member. The pin has a non-circular cross-section.

8 Claims, 6 Drawing Sheets

U.S. PATENT DOCUMENTS

| | | |
|---|---|---|
| 4,566,620 A | 1/1986 | Greene et al. |
| 4,568,009 A | 2/1986 | Green |
| 4,573,622 A | 3/1986 | Green et al. |
| 4,580,712 A | 4/1986 | Green |
| 4,585,153 A | 4/1986 | Failla et al. |
| 4,589,582 A | 5/1986 | Bilotti |
| 4,602,634 A | 7/1986 | Barkley |
| 4,605,001 A | 8/1986 | Rothfuss et al. |
| 4,605,004 A | 8/1986 | DiGiovanni et al. |
| 4,606,344 A | 8/1986 | DiGiovanni |
| 4,606,345 A | 8/1986 | Dorband et al. |
| 4,607,636 A | 8/1986 | Kula et al. |
| 4,612,933 A | 9/1986 | Brinkerhoff et al. |
| 4,617,928 A | 10/1986 | Alfranca |
| 4,632,290 A | 12/1986 | Green et al. |
| 4,665,916 A | 5/1987 | Green |
| 4,684,051 A | 8/1987 | Akopov et al. |
| 4,714,187 A | 12/1987 | Green |
| 4,715,520 A | 12/1987 | Roehr, Jr. et al. |
| 4,728,020 A | 3/1988 | Green et al. |
| 4,767,044 A | 8/1988 | Green |
| 4,788,978 A | 12/1988 | Strekopytov et al. |
| 4,802,614 A | 2/1989 | Green et al. |
| 4,805,823 A | 2/1989 | Rothfuss |
| 4,819,853 A | 4/1989 | Green |
| 4,848,637 A | 7/1989 | Pruitt |
| 4,869,414 A | 9/1989 | Green et al. |
| 4,881,544 A | 11/1989 | Green et al. |
| 4,881,545 A | 11/1989 | Isaacs et al. |
| 4,915,100 A | 4/1990 | Green |
| 4,930,503 A | 6/1990 | Pruitt |
| 4,938,408 A | 7/1990 | Bedi et al. |
| 4,941,623 A | 7/1990 | Pruitt |
| 4,951,861 A | 8/1990 | Schulze et al. |
| 4,964,559 A | 10/1990 | Deniega et al. |
| 5,005,754 A | 4/1991 | Van Overloop |
| 5,018,657 A | 5/1991 | Pedlick et al. |
| 5,071,052 A | 12/1991 | Rodak et al. |
| 5,100,042 A | 3/1992 | Gravener et al. |
| 5,116,349 A | 5/1992 | Aranyi |
| 5,137,198 A | 8/1992 | Nobis et al. |
| 5,172,845 A | 12/1992 | Tejeiro |
| 5,190,203 A | 3/1993 | Rodak |
| 5,219,111 A | 6/1993 | Bilotti et al. |
| 5,240,163 A | 8/1993 | Stein et al. |
| 5,344,060 A | 9/1994 | Gravener et al. |
| 5,368,599 A | 11/1994 | Hirsch et al. |
| 5,405,073 A | 4/1995 | Porter |
| 5,413,267 A | 5/1995 | Solyntjes et al. |
| 5,439,155 A | 8/1995 | Viola |
| 5,452,836 A | 9/1995 | Huitema et al. |
| 5,458,279 A | 10/1995 | Plyley |
| 5,462,215 A | 10/1995 | Viola et al. |
| 5,464,144 A | 11/1995 | Guy et al. |
| 5,465,894 A | 11/1995 | Clark et al. |
| 5,470,006 A | 11/1995 | Rodak |
| 5,470,008 A | 11/1995 | Rodak |
| 5,470,009 A | 11/1995 | Rodak |
| 5,497,934 A | 3/1996 | Brady et al. |
| 5,503,320 A | 4/1996 | Webster et al. |
| 5,509,596 A | 4/1996 | Green et al. |
| 5,542,594 A | 8/1996 | McKean et al. |
| 5,547,117 A | 8/1996 | Hamblin et al. |
| 5,558,266 A | 9/1996 | Green et al. |
| 5,579,978 A | 12/1996 | Green et al. |
| 5,580,067 A | 12/1996 | Hamblin et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,615,820 A | 4/1997 | Viola |
| 5,641,111 A | 6/1997 | Ahrens et al. |
| 5,678,748 A | 10/1997 | Plyley et al. |
| 5,697,543 A | 12/1997 | Burdorff |
| 5,706,997 A | 1/1998 | Green et al. |
| 5,706,998 A | 1/1998 | Plyley et al. |
| 5,732,871 A | 3/1998 | Clark et al. |
| 5,735,445 A | 4/1998 | Vidal et al. |
| 5,772,099 A | 6/1998 | Gravener |
| 5,794,834 A | 8/1998 | Hamblin et al. |
| 5,810,240 A | 9/1998 | Robertson |
| 5,855,311 A | 1/1999 | Hamblin et al. |
| 5,878,937 A | 3/1999 | Green et al. |
| 5,893,506 A | 4/1999 | Powell |
| 5,894,979 A | 4/1999 | Powell |
| 5,964,394 A | 10/1999 | Robertson |
| 6,045,560 A | 4/2000 | McKean et al. |
| 6,638,285 B2 | 10/2003 | Gabbay |
| 6,805,273 B2 | 10/2004 | Bilotti et al. |
| 6,817,508 B1 | 11/2004 | Racenet et al. |
| 6,988,650 B2 | 1/2006 | Schwemberger et al. |
| 7,070,083 B2 | 7/2006 | Jankowski |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,210,609 B2 | 5/2007 | Leiboff et |
| 7,237,708 B1 | 7/2007 | Guy et al. |
| 7,275,674 B2 | 10/2007 | Racenet et al. |
| RE40,237 E | 4/2008 | Bilotti et al. |
| 7,407,076 B2 | 8/2008 | Racenet et al. |
| 7,431,190 B2 | 10/2008 | Hoffman |
| 7,522,854 B2 | 4/2009 | Kinouchi et al. |
| 7,549,563 B2 | 6/2009 | Mather et al. |
| 7,568,605 B2 | 8/2009 | Kruszynski |
| 7,641,092 B2 | 1/2010 | Kruszynski et al. |
| 7,988,028 B2 * | 8/2011 | Farascioni et al. .......... 227/180.1 |
| 8,033,439 B2 * | 10/2011 | Racenet et al. ............ 227/176.1 |
| 8,136,712 B2 * | 3/2012 | Zingman .................... 227/179.1 |
| 2004/0084505 A1 | 5/2004 | Bilotti et al. |
| 2004/0164123 A1 | 8/2004 | Racenet et al. |
| 2005/0247752 A1 | 11/2005 | Kelly et al. |
| 2005/0247753 A1 | 11/2005 | Kelly et al. |
| 2006/0163312 A1 | 7/2006 | Viola et al. |
| 2006/0201992 A1 | 9/2006 | Racenet et al. |
| 2006/0273135 A1 | 12/2006 | Beetel |
| 2007/0029364 A1 | 2/2007 | Kruszynski et al. |
| 2007/0039996 A1 | 2/2007 | Mather et al. |
| 2007/0039997 A1 | 2/2007 | Mather et al. |
| 2007/0095877 A1 | 5/2007 | Racenet et al. |
| 2007/0187456 A1 | 8/2007 | Viola et al. |
| 2007/0221702 A1 | 9/2007 | Kruszynski |
| 2007/0262116 A1 | 11/2007 | Hueil |
| 2008/0023523 A1 | 1/2008 | Racenet et al. |
| 2008/0093415 A1 | 4/2008 | Bilotti |
| 2009/0255976 A1 | 10/2009 | Marczyk et al. |
| 2009/0261143 A1 | 10/2009 | Wixey et al. |
| 2009/0277948 A1 | 11/2009 | Beardsley et al. |
| 2009/0302092 A1 | 12/2009 | Kasvikis et al. |
| 2009/0302093 A1 | 12/2009 | Kasvikis |
| 2010/0038403 A1 | 2/2010 | D'Arcangelo |
| 2010/0048988 A1 | 2/2010 | Pastorelli et al. |

\* cited by examiner

PIN LOCKING MECHANISM FOR A SURGICAL INSTRUMENT

This application claims priority from provisional application Ser. No. 61/175,815, filed May 6, 2009, the entire contents of which are incorporated herein by reference.

BACKGROUND

1. Technical Field

The present disclosure relates generally to a surgical instrument and, more specifically, to a surgical instrument for clamping, severing, and joining tissue.

2. Background of Related Art

Certain surgical stapling instruments are used for applying rows of staples through compressed living tissue. These surgical stapling instruments are employed, for example, for fastening tissue or organs prior to transection or resection or during anastomoses. In some cases, these surgical stapling instruments are utilized for occluding organs in thoracic and abdominal procedures.

Typically, such surgical stapling instruments include an anvil assembly, a cartridge assembly for supporting an array of surgical staples, an approximation mechanism for approximating the cartridge and anvil assemblies, an alignment or guide pin assembly for capturing tissue between the cartridge and anvil assemblies and for maintaining alignment between the cartridge and anvil assemblies during approximation and firing, and a firing mechanism for ejecting the surgical staples from the cartridge assembly.

In use, the alignment pin assembly is advanced and the anvil and cartridge assemblies are approximated. Next, the surgeon tires the instrument to place staples in tissue. Optionally, the surgeon may use the same instrument or a separate device to cut the tissue adjacent or between the row(s) of staples. The alignment pin in some instances is advanced automatically with approximation of the cartridge; in other instances it is advanced by a separate mechanism.

SUMMARY

The present disclosure provides a surgical instrument comprising a handle portion, an elongated portion defining a longitudinal axis and extending distally from the handle portion, and an end effector disposed adjacent a distal portion of the elongated portion including a first jaw member and a second jaw member dimensioned to clamp tissue therebetween.

A pin is disposed in mechanical cooperation with the first jaw member and includes an engagement section and is movable between a first position wherein the engagement section is spaced from the second jaw member and a second position wherein the engagement section engages the second jaw member. The pin has a non-circular cross-section.

Preferably, a knife is provided to move distally to cut the clamped tissue. Preferably, the knife has an upper edge terminating alongside the pin. In one embodiment, the pin has a gap dimensioned to accommodate the knife. The instrument can include rows of fasteners with the knife positioned between the rows.

In one embodiment, the pin is substantially semi-circular in cross-section. In another embodiment the pin is substantially L-shaped in cross-section.

The instrument can include a second non-circular pin. In one embodiment, the pins are spaced from each other and one pin is adjacent a top portion of a knife and the other pin is positioned adjacent a bottom portion of the knife. The pins can be positioned on opposite sides of a knife slot from which the knife extends.

In some embodiments, the instrument can further include a second pin having a substantially semi-circular cross section, each of the pins having a substantially planar surface, the substantially planar surface of the second pin facing a direction opposite the direction the substantially planar surface the other pin faces.

The pins in some embodiments can move in a distal direction automatically when the first and second jaw members move to a position to clamp tissue.

In another aspect, a surgical instrument is provided comprising a handle portion, an elongated portion defining a longitudinal axis and extending distally from the handle portion, and an end effector disposed adjacent a distal portion of the elongated portion. The end effector included a first jaw member and a second jaw member, the first and second jaw members dimensioned to clamp tissue therebetween. The first jaw member has at least one row of fasteners arranged in a row substantially transverse to the longitudinal axis. A pin is disposed in mechanical cooperation with the first jaw member and includes an engagement section, the pin movable between a first position wherein the engagement section is spaced from the second jaw member and a second position wherein the engagement section engages the second jaw member. A second pin is spaced from the first pin, the first pin and second pin each having a surface alongside the knife wherein the first surface of the first pin faces in a first direction and the second surface of the second pin faces in a second opposite direction.

In some embodiments, the first and second surfaces of the pins are substantially planar. The first pin can have a third surface facing toward a top surface of the knife and the second pin can have a fourth surface facing towards the bottom surface of the knife. In some embodiments, the pins move in a distal direction automatically when the first and second jaw members move to a position to clamp tissue.

BRIEF DESCRIPTION OF DRAWINGS

Various embodiments of the presently disclosed surgical stapling instrument are disclosed herein with reference to the drawings, wherein.

DETAILED DESCRIPTION OF THE EMBODIMENTS

Figure 1:
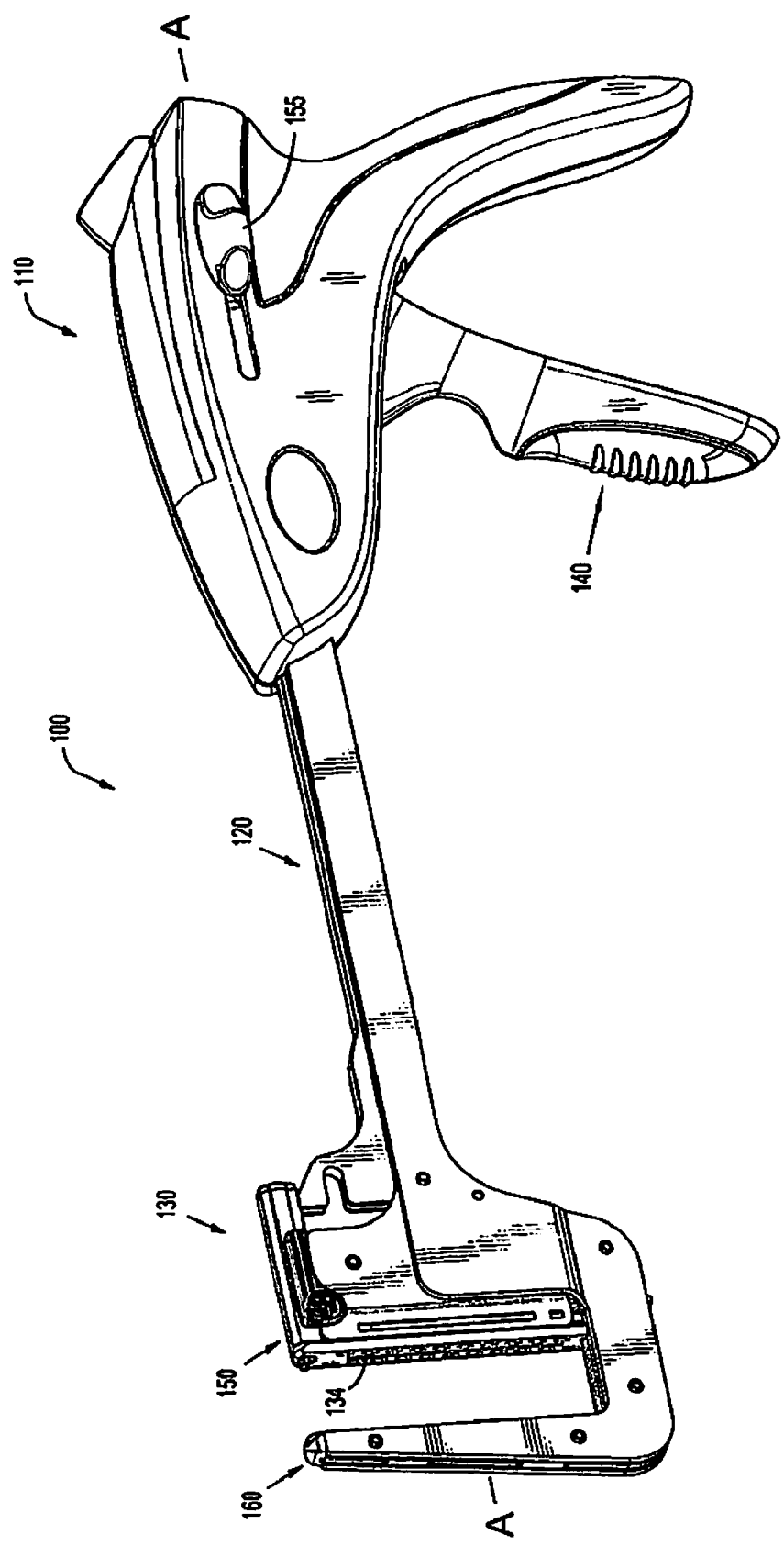
FIG. 1 is a perspective view of a surgical stapling instrument of the present disclosure.

Embodiments of the presently disclosed surgical stapling instrument are described in detail with reference to the drawings, wherein like reference numerals designate corresponding elements in each of the several views. In the description that follows, the term "proximal" refers to the end or portion of the surgical stapling instrument closer to the user, whereas the term "distal" refers to the end or portion of the surgical stapling instrument further from the user.

In the interest of brevity, the present disclosure focuses on the pin for a surgical stapling instrument designated in the drawings by reference numeral 100. U.S. Pat. No. 7,407,076, the entire contents of which are incorporated by reference herein, describes in detail the structure and operation of an embodiment of surgical stapling instrument 100.

FIG. 1 illustrates a surgical stapling instrument 100 designed for applying fasteners and cutting tissue. In brief, surgical stapling instrument 100 includes a handle portion 110, an elongate portion 120, and an end effector 130 extending from the distal portion of the elongate portion 120. Handle portion 110 contains a trigger 140 for actuating end effector 130. Elongate portion 120 extends distally from handle portion 110 and defines a longitudinal axis A-A therealong. End effector 130 is disposed adjacent to a distal portion of elongate portion 120 and includes a first jaw member or cartridge assembly 150 and a second jaw member or anvil assembly 160. In this embodiment, cartridge assembly 150 is adapted to move longitudinally with respect to anvil assembly 160 upon actuation of trigger 140 to clamp tissue between the jaw members 150, 160. It is also contemplated that the anvil assembly can be moved (approximated) toward the cartridge assembly or that the cartridge and anvil assemblies can both be moved toward each other to clamp tissue.

Cartridge assembly 150 includes a plurality of slots 152 (FIGS. 1B and 1C) each capable of holding a staple or any other suitable fastener. Each slot 152 is operatively associated with a pusher thrust bar or plunger 122. Pusher 122 extends along elongate portion 120 and partially into cartridge assembly 150. Cartridge assembly 150 also includes a knife advanceable to cut tissue clamped between the cartridge and anvil assemblies 150, 160, respectively. In use, pusher 122 moves distally upon actuation of trigger 140 and causes the ejection of the staples disposed in slots 152 in a distal direction, substantially parallel to the longitudinal axis of the elongate portion 120. In addition to slots 152, cartridge assembly 150 includes a pin 154 operatively connected to pusher 122 and a bore 156 dimensioned to slidably receive pin 154. Pin 154 is adapted to move longitudinally along bore 156 in response to a translation of pusher 122. The pin 154 can alternatively be moved by a sliding knob 155 in the handle portion 110. In the embodiment depicted in FIG. 1A-1C, anvil assembly 160 has a hole 162 designed to receive at least a portion of pin 154. Anvil assembly 160 has staple-deforming pockets 164 for deforming the fasteners ejected from cartridge assembly 150. An elongated slot can be provided between the pockets 164 in the anvil assembly to accommodate the knife described below.

Figure 1B:
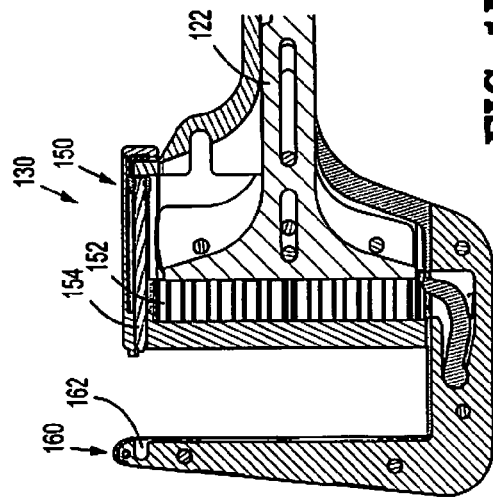
FIG. 1B is a side cross-sectional view of the end effector of the instrument of FIG. 1 with the jaw members in the open position.
Figure 1C:
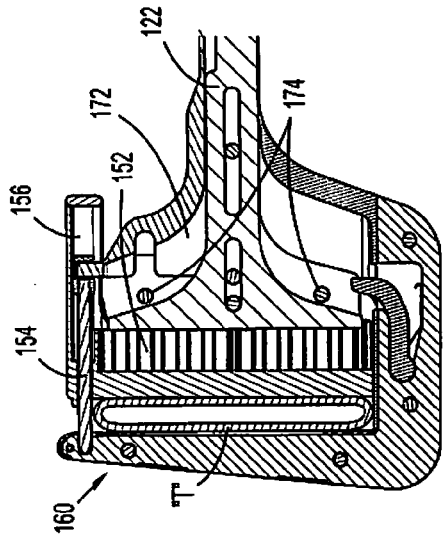
FIG. 1C is a side cross-sectional view of the end effector of FIG. 1 with the jaw members in the closed position.
Figure 1A:
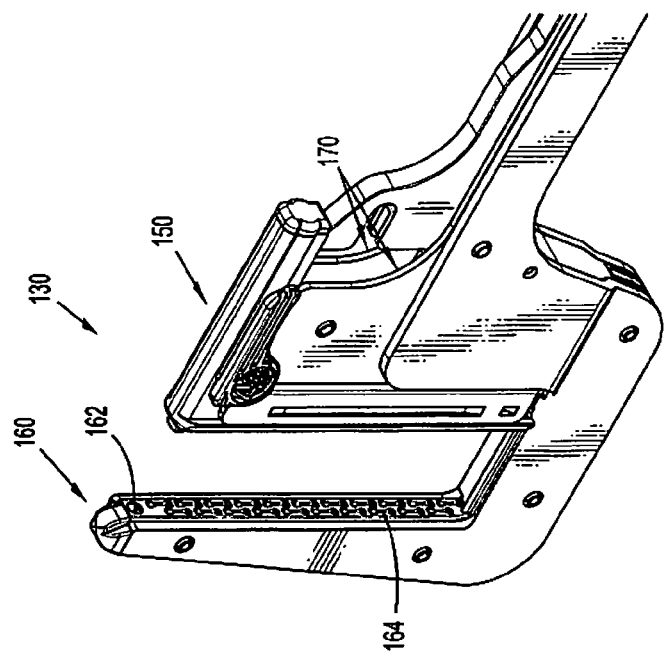
FIG. 1A is a perspective view of an end effector of the instrument of FIG. 1.

While anvil assembly 160 remains stationary with respect to cartridge assembly 150 during operation, cartridge assembly 150 is movable longitudinally between a proximal position and a distal position upon actuation of trigger 140. In the proximal position, cartridge assembly 150 is spaced apart from anvil assembly 160, as seen in FIG. 1B in an approximated position. The actuation of trigger 140 causes clamp slides 170, operatively connected thereto, to move distally which in turn causes thrust bar 122 to move distally due to pins 174. In turn, the distal translation of thrust bar 122 causes the distal movement of cartridge assembly 150 toward anvil assembly 160 to an approximated position. While cartridge assembly 150 moves from the proximal position toward the distal position, end effector 130 clamps any tissue placed between cartridge assembly 150 and anvil assembly 160 as shown in FIG. 1C. In the distal position, cartridge assembly 150 is located closer to anvil assembly 160 and presses tissue "T" against anvil assembly 160.

Further actuation of trigger 140, i.e. a second squeeze of the trigger 140, once cartridge assembly 150 reaches its distal (approximated) position causes ejection of the fasteners from slots 152. That is, the continued distal translation of pusher 122, once cartridge assembly 150 is located in the distal position, causes the deployment of the fasteners positioned in slots 152. During deployment, these fasteners exit slots 152 and advance through tissue and into contact with staple-deforming pockets 164 of anvil assembly 160 for formation thereof, e.g. bending of the staple legs into a "B" configuration. Actuation of trigger 140 also advances the knife to sever tissue clamped between the cartridge and anvil jaw assemblies 150, 160.

Note the distal motion of clamp slides 170 causes alignment pin 154 to move distally along bore 156 due to the operative connection of the alignment pin pusher 172 to the clamp slides 170 via pins extending through elongated slots in pin pusher 172 as described in U.S. Pat. No. 7,407,076. (Pin pusher 172 includes a vertical portion having an abutment member configured to engage the proximal end of the pin 154.) Upon sufficient distal movement of pin 154, hole 162 of anvil assembly 160 receives a portion of pin 154. The structural interaction between pin 154 and hole 162 (when cartridge assembly 150 is located in the distal position) assists in the alignment of slots 152 with staple-deforming pockets 164. It should be appreciated that alignment pin 154 can alternatively be moved manually as pin pusher 172 is moved manually, e.g. by sliding knob 155.

Turning now to embodiments of the alignment pins of the present disclosure illustrated in FIGS. 2-7, these pins can be used with the stapler of FIG. 1 described above or with other suitable surgical staplers. They can be configured to move automatically with approximation of the cartridge, i.e. in response to actuation of the trigger, and/or moved by the user separate from approximation, e.g. by an independent slidable knob or other manual controls or knobs located at various portions of the instrument. Thus, it should be understood that it is contemplated that the pins disclosed herein can be moved in either way (automatic or manual) or in both ways.

Figure 3:
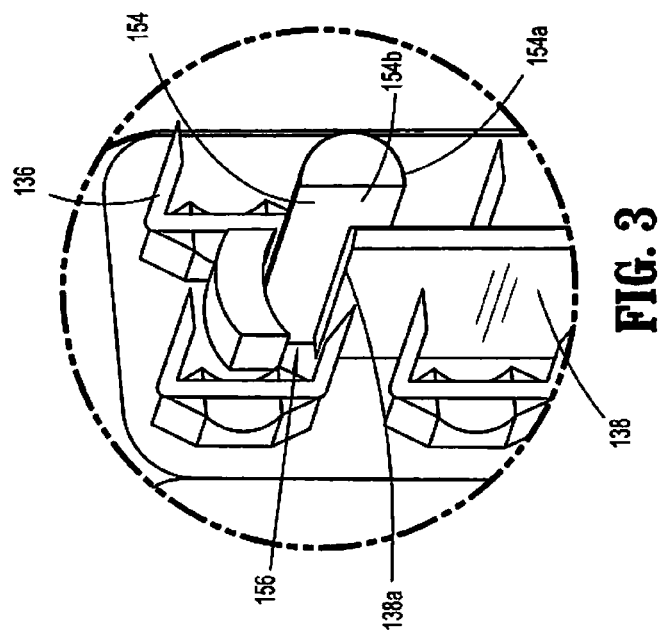
FIG. 3 is a perspective view of the area of detail designated in FIG. 2.
Figure 2:
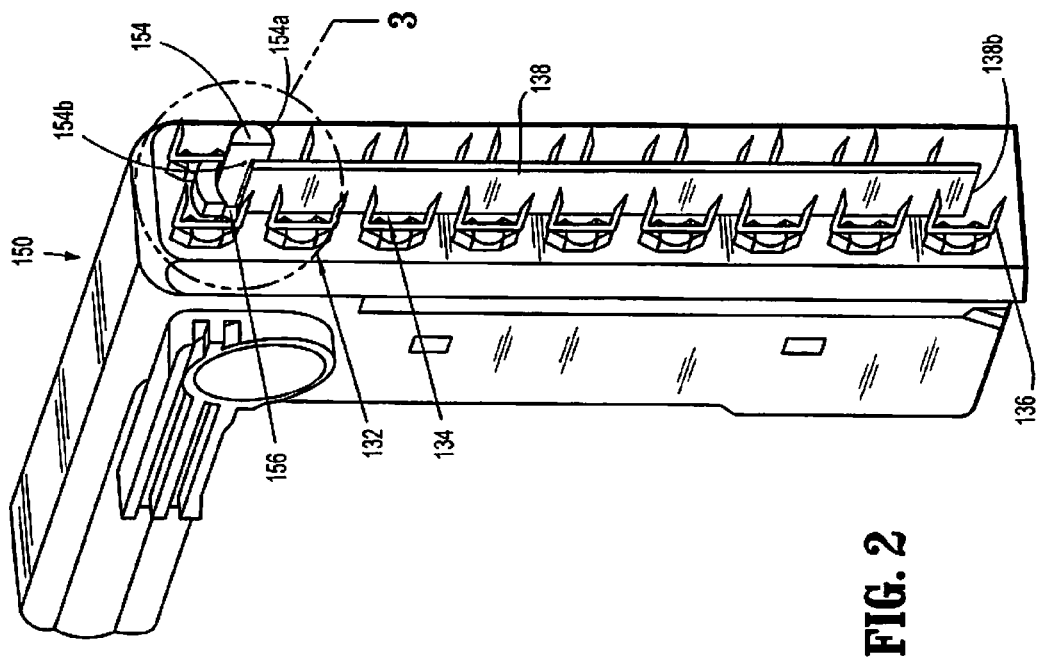
FIG. 2 is a close up perspective view of one embodiment of the cartridge assembly having a pin with a semi-circular cross-section.

FIGS. 2 and 3 illustrate a close up view of the cartridge assembly 150 of FIG. 1. In this embodiment, cartridge assembly 150 includes a plurality of staple slots 132 and a knife slot 134. Each staple slot 132 houses a staple or fastener 136. Knife slot 134 is adapted to receive knife 138. Knife 138 is configured to move longitudinally to cut tissue between the staple rows. Preferably, knife 138 is advanced distally when the staples are advanced from cartridge assembly 150 through tissue. In this embodiment, two rows of staples are provided, extending substantially linearly and substantially transverse to longitudinal axis A-A of the instrument 100. A different number of staples and staple rows are also contemplated.

Cartridge assembly 150 further includes a bore 156 configured to receive a pin 154. Pin 154 is adapted to move longitudinally between a proximal position and a distal position and has a substantially semi-circular cross-section to allow passage of knife 138 adjacent the pin 154. That is, the knife 138 passes by (alongside) the substantially planar inner surface region of the pin 154. The substantially semi-circular shape of pin 154 allows the knife 138 to extend up to the region of the pin 154. As shown, the knife 134 extends past the bottom 154a of the pin 154 and terminates adjacent an intermediate region 154b of the pin 154. Other knife heights are also contemplated. The staple slots 156 and staple line extend beyond the top edge 138a of the knife 138 and beyond the bottom edge 138b of the knife 138.

Figure 4:
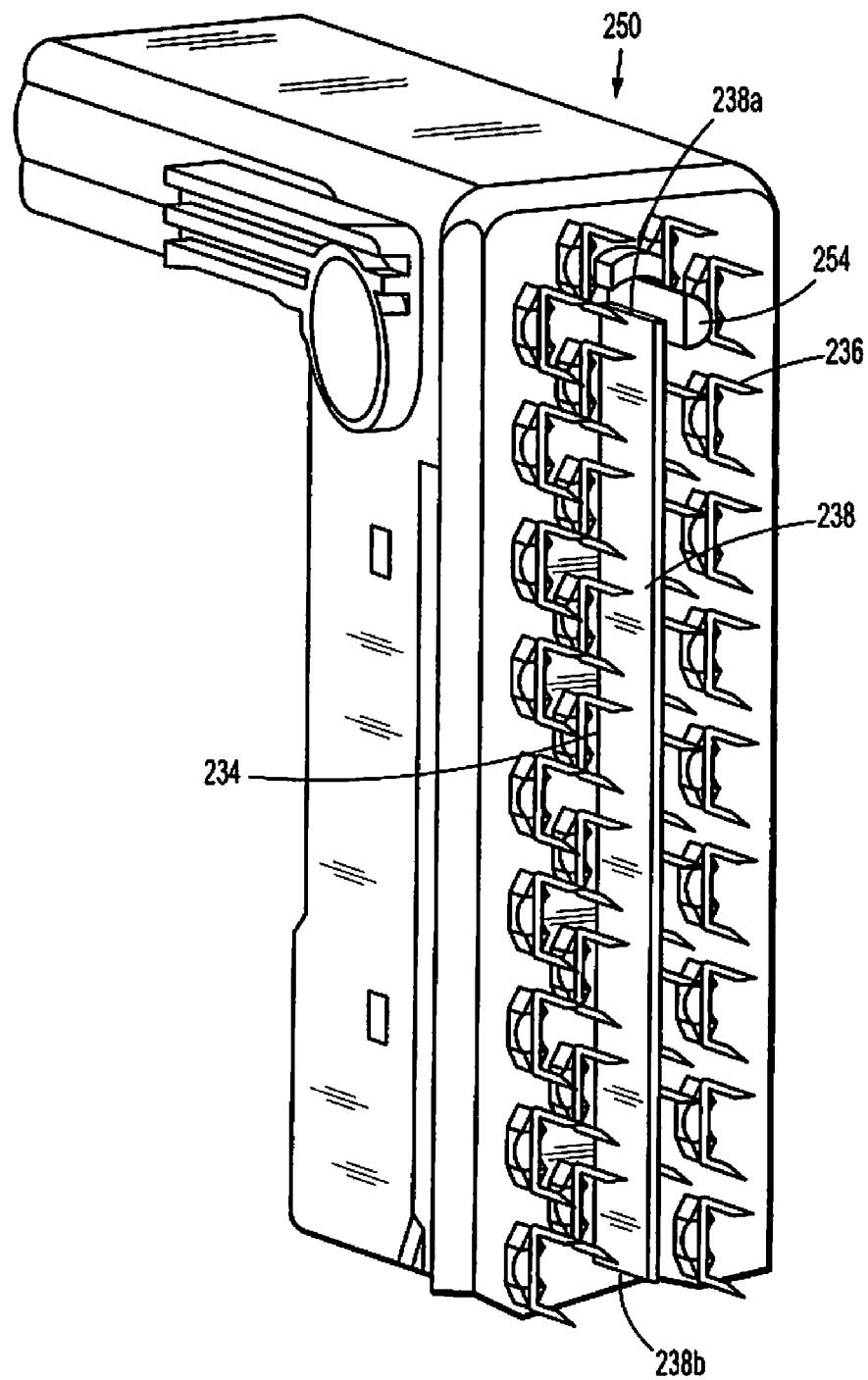
FIG. 4 a close up perspective view of another embodiment of the cartridge assembly having four rows of staples.
Figure 6:
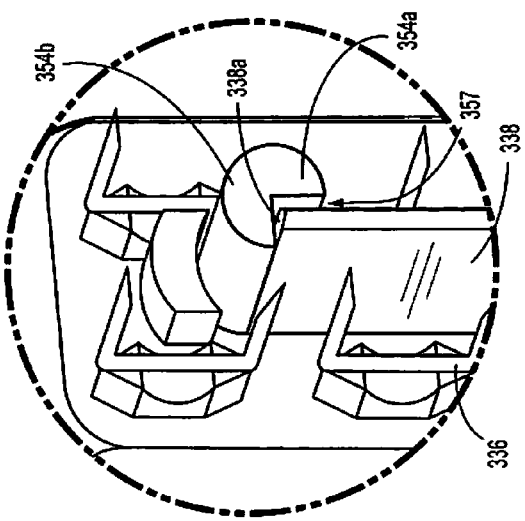
FIG. 6 is a close up perspective view of the area of detail designated in FIG. 5.

FIG. 4 illustrates an alternate embodiment of the cartridge assembly, designated generally by reference numeral 250. Cartridge assembly is substantially identical to cartridge assembly 150 of FIG. 2, except that four rows of staples are provided. As shown, the four substantially linear rows of staples 236 are arranged substantially transverse to the longitudinal axis A-A of the instrument, with two staggered rows positioned on either side of knife 238. As in the other embodiments herein, the staples 236 are fired in a direction substantially parallel to the longitudinal axis of the instrument. The knife 238 is movable from knife slot 234 to sever tissue clamped between the cartridge and anvil assemblies. Pin 254 is substantially semi-circular shaped, similar to pin 154. The staples 236 extend beyond the upper and lower edges 238a, 238b, respectively, of knife 238.

Figure 5:
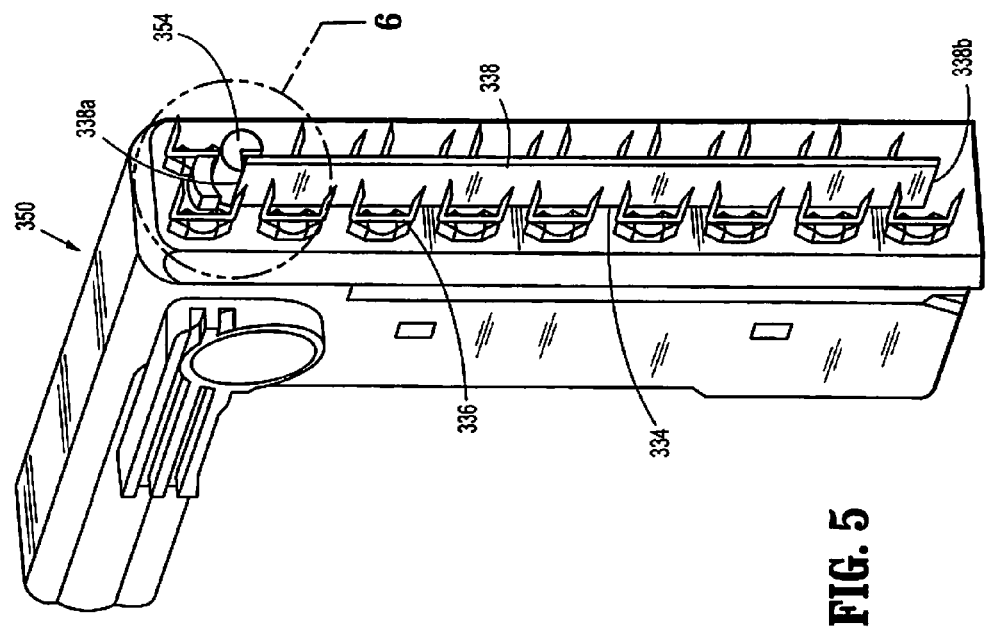
FIG. 5 is a close up perspective view of another embodiment of the cartridge assembly.
Figure 7:
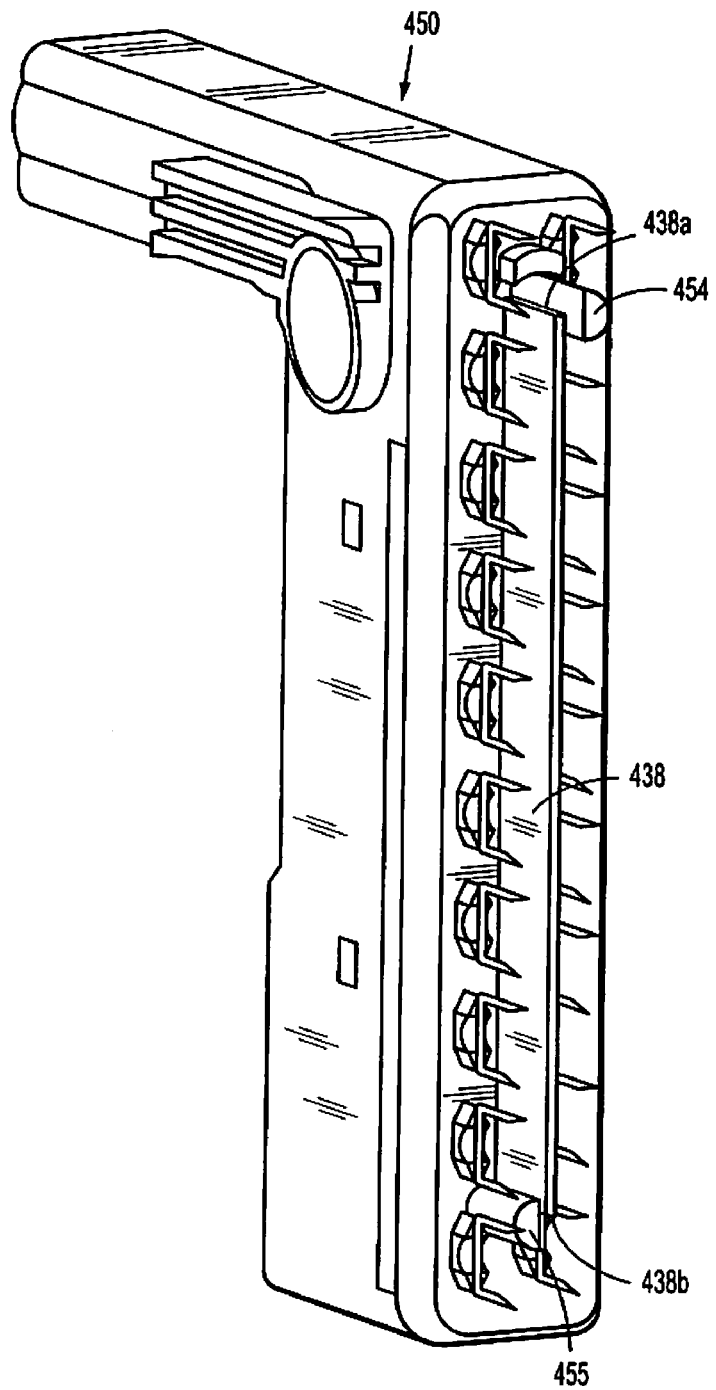
FIG. 7 is a close up perspective view of another embodiment of the cartridge assembly having two pins with a semicircular cross-section.

In the alternate embodiment of FIG. 5, cartridge assembly, designated generally by reference numeral 350, is substantially identical to cartridge assembly 150 of FIG. 2, except for the configuration of pin 354. As shown, two substantially linear rows of staples 236 are arranged substantially transverse to the longitudinal axis of the instrument, with one row positioned on either side of knife 338. A different number of rows are also contemplated. The knife 338 is movable from knife slot 334 to sever tissue clamped between the cartridge and anvil assemblies. The staples 336 extend beyond the upper and lower edges 338a, 338b, respectively, of knife 338. Pin 354 is substantially L-shaped in configuration to create a gap 357 to accommodate the knife. That is, portion 354a extends downwardly alongside the knife 338 and portion 354b extends transversely above the upper edge 338a of knife 338. Consequently, the pin 354 extends in an arc of about 270 degrees (although other arcs are also contemplated).

It should be appreciated that although one alignment pin is shown, it is also contemplated that two alignment pins can be provided, e.g. one on the upper portion of the cartridge and the other on the lower portion of the cartridge. This is shown for example in the embodiment of FIG. 7, wherein upper pin 454 and lower pin 455 are provided in cartridge 450. Each of the pins 454, 455 are substantially semi-circular in configuration, similar to pin 254 of FIG. 2, however the substantially L-shaped pins of FIG. 5 could also be provided (either one at the top or bottom utilized with the substantially semi-circular pin on the opposing end or on both the top and bottom.) Note that the pins 454, 455 are preferably on opposing sides of the knife 438. As in the other embodiments, the staple line extends beyond the upper edge 438a and lower edge 438b of knife 438.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the claims appended hereto.

What is claimed is:

1. A surgical instrument, comprising:
   a handle portion;
   an elongated portion defining a longitudinal axis and extending distally from the handle portion;
   an end effector disposed adjacent a distal portion of the elongated portion, the end effector including a first jaw member and a second jaw member, the first and second jaw members dimensioned to clamp tissue therebetween, the first jaw member having at least one row of fasteners arranged in a row substantially transverse to the longitudinal axis;
   first and second pins disposed in mechanical cooperation with the first jaw member, each pin including an engagement section, the first and second pins movable between a first position wherein the engagement section is spaced from the second jaw member and a second position wherein the engagement section engages the second jaw member, wherein each pin has a semi-circular cross-section, the first and second pins spaced from each other; and
   a knife movable between distal and proximal portions, the knife having an upper edge terminating alongside the first pin and a lower edge terminating alongside the second pin, a planar surface of the first pin located on a first side of the knife and a planar surface of the second pin located on a second side of the knife that is opposite the first side such that the planar surfaces of the pins are oriented towards each other.

2. The surgical instrument of claim 1, further comprising two rows of fasteners, the knife positioned between the two rows of fasteners.

3. The surgical instrument of claim 1, wherein the pins move in a distal direction automatically when the first and second jaw members move to a position to clamp tissues.

4. The surgical instrument of claim 1, wherein each pin is substantially D-shaped.

5. The surgical instrument of claim 1, wherein the planar surface of the first pin is oriented towards the first side of the knife and the planar surface of the second pin is oriented towards the second side of the knife.

6. The surgical instrument of claim 5, wherein the first side of the knife faces one planar surface of the first and second pins.

7. The surgical instrument of claim 1, wherein the planar surface of each pin is oriented towards the knife and a hemispherical portion of each pin extends away from the knife.

8. The surgical instrument of claim 1, wherein the knife defines a longitudinal axis between the upper edge and the lower edge, each pin positioned such that the planar surface of each pin does not extend across the longitudinal axis.

* * * * *